United States Patent
Choi

(10) Patent No.: US 9,596,991 B2
(45) Date of Patent: Mar. 21, 2017

(54) SELF-EXAMINATION APPARATUS AND METHOD FOR SELF-EXAMINATION

(75) Inventor: Kyuhyoung Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 1730 days.

(21) Appl. No.: 13/056,125

(22) PCT Filed: Sep. 9, 2010

(86) PCT No.: PCT/KR2010/006122
§ 371 (c)(1),
(2), (4) Date: Jan. 27, 2011

(87) PCT Pub. No.: WO2012/033244
PCT Pub. Date: Mar. 15, 2012

(65) Prior Publication Data
US 2012/0065476 A1    Mar. 15, 2012

(51) Int. Cl.
*G06F 19/00* (2011.01)
*A61B 5/00* (2006.01)

(52) U.S. Cl.
CPC .......... *A61B 5/0022* (2013.01); *A61B 5/0013* (2013.01); *A61B 5/743* (2013.01); *G06F 19/345* (2013.01); *G06F 19/3406* (2013.01); *G06F 19/363* (2013.01)

(58) Field of Classification Search
None
See application file for complete search history.

(56) References Cited

U.S. PATENT DOCUMENTS

| | | | |
|---|---|---|---|
| 5,551,436 A | 9/1996 | Yago | |
| 6,022,315 A * | 2/2000 | Iliff | 600/300 |
| 6,889,137 B1 * | 5/2005 | Rychlak | G01C 21/3407 340/286.07 |
| 2003/0139652 A1 | 7/2003 | Kang et al. | |
| 2005/0015115 A1 * | 1/2005 | Sullivan et al. | 607/5 |
| 2006/0047188 A1 * | 3/2006 | Bohan | 600/300 |
| 2006/0111749 A1 * | 5/2006 | Westenskow et al. | 607/5 |
| 2007/0073113 A1 * | 3/2007 | Squilla et al. | 600/300 |
| 2008/0082659 A1 * | 4/2008 | Haslehurst et al. | 709/224 |
| 2008/0269571 A1 * | 10/2008 | Brown et al. | 600/300 |
| 2009/0131759 A1 * | 5/2009 | Sims et al. | 600/301 |
| 2009/0240524 A1 * | 9/2009 | Bluth | 705/2 |
| 2010/0332250 A1 * | 12/2010 | Simpson et al. | 705/2 |
| 2011/0130635 A1 * | 6/2011 | Ross | 600/301 |

FOREIGN PATENT DOCUMENTS

| | | |
|---|---|---|
| JP | 7-95961 A | 4/1995 |
| JP | 11-347003 A | 12/1999 |
| JP | 2000-197612 A | 7/2000 |

* cited by examiner

*Primary Examiner* — William Thomson
*Assistant Examiner* — Davin Sands
(74) *Attorney, Agent, or Firm* — Birch, Stewart, Kolasch & Birch, LLP

(57) ABSTRACT

The present invention relates to an apparatus and a method for a self-examination. And more particularly, the present invention relates to an apparatus and a method providing examination guide information for the self-examination.

15 Claims, 20 Drawing Sheets

Please answer to the following questions.

1. Do you have a fever?        ①Yes ②No

2. Do you have sore eyes?      ①Yes ②No

3. Do you have a stomachache?  ①Yes ②No

4. Do you feel dizzy?          ①Yes ②No

5. Do you have a cough?        ①Yes ②No

> Please choose one or more suspected diseases from the following.
>
> 1. Head cold
>
> 2. Sore throat
>
> 3. Illness from fatigue
>
> 4. Diabetes
>
> 5. High blood pressure
>
>     .
>     .
>     .

(a)

(b)

SELF-EXAMINATION APPARATUS AND METHOD FOR SELF-EXAMINATION

TECHNICAL FIELD

The present invention relates to an apparatus and a method for a self-examination. And more particularly, the present invention relates to an apparatus and a method providing examination guide information for the self-examination.

BACKGROUND ART

As society is advancing, people are increasingly interested in their health, and in line with this, demand for medical services is increasing. However, the busy life in modern society makes it ineffective and difficult for people to get medical services from doctors in terms of costs and realistically, so the necessity of an alternative medical service has emerged.

DISCLOSURE

Technical Problem

Therefore, the present invention has been devised to address the above matters, and various features described herein have been conceived.

An aspect of the present invention provides an apparatus and a method for a self-examination for guiding a user to examine himself.

Another aspect of the present invention provides an apparatus and a method for a self-examination allowing a user to perform a customized self-examination according to his physical condition.

Another aspect of the present invention provides an apparatus and a method for a self-examination for guiding a user to manipulate a medical examination instrument.

Another aspect of the present invention provides an apparatus and a method for a self-examination for allowing a user to provide the results of self-examination to a doctor.

Technical ideas devised by the present invention are not limited to those described above and any other technical ideas not mentioned could be clearly understood by a person skilled in the art to which the present invention pertains from the following description.

Technical Solution

The present invention provides an apparatus and a method for a self-examination to solve the foregoing problems.

According to an aspect of the present invention, there is provided an apparatus for a self-examination comprising: an output unit configured to display an patient image; a communication unit; and a controller configured to: obtain medical examination guide information based on at least one of a symptom and a suspected disease, wherein the medical examination guide information includes information of a body part; control the output unit to display an icon for the self-examination on the patient image at a position corresponding to the body part, and receive, via the communication unit, examination data from a medical examination instrument which obtains the examination data from the body part.

According to another aspect of the present invention, there is provided an apparatus for a self-examination comprising: an input unit; an output unit configured to display an patient image; a communication unit; and a controller configured to: control the output unit to output a symptom survey, and receives, via the input unit, a reply to the symptom survey; the obtain medical examination guide information based on at least one of a symptom and a suspected disease, wherein the medical examination guide information includes information of a body part; control the output unit to display an icon for the self-examination on the patient image at a position corresponding to the body part, and receive, via the communication unit, examination data from a medical examination instrument which obtains the examination data from the body part.

According to another aspect of the present invention, there is provided an apparatus for a self-examination comprising: an output unit configured to display an patient image; a communication unit; and a controller configured to: obtain medical examination guide information based on at least one of a symptom and a suspected disease, wherein the medical examination guide information includes information of a body part and information of a medical examination instrument; control the output unit to display an icon for the self-examination on the patient image at a position corresponding to the body part, receive, via the communication unit, examination data from the medical examination instrument which obtains the examination data from the body part, and when the medical examination instrument from which the apparatus received the medical examination data is different from the medical examination instrument according to the medical examination guide information, control the output unit to output an error message.

According to another aspect of the present invention, there is provided an apparatus for a self-examination comprising: an output unit configured to display an patient image; a communication unit; and a controller configured to: obtain medical examination guide information based on at least one of a symptom and a suspected disease, wherein the medical examination guide information includes information of a body part; control the output unit to display an icon for the self-examination on the patient image at a position corresponding to the body part, when the medical examination instrument is on the body part, the controller controls the output unit to output an alarm message, and receive, via the communication unit, examination data from a medical examination instrument which obtains the examination data from the body part.

According to another aspect of the present invention, there is provided an apparatus for a self-examination comprising: an output unit configured to display an patient image; a communication unit; and a controller configured to: obtain medical examination guide information based on at least one of a symptom and a suspected disease, wherein the medical examination guide information includes information of a body part; control the output unit to display an icon for the self-examination on the patient image at a position corresponding to the body part, receive, via the communication unit, examination data from a medical examination instrument which obtains the examination data from the body part, and determine a presumed disease considering at least one of the symptom, the suspected disease and the medical examination data.

According to another aspect of the present invention, there is provided an apparatus for a self-examination comprising: an output unit configured to: display a patient image, and output a symptom survey; an input unit configured to receive a reply to the survey; a communication unit configured to: transmit the reply to an external device, and receive medical examination guide information including information of a body part from the external device; and a controller configured to: control the output unit to display an icon for the self-examination on the patient image at a position corresponding to the body part, and receives, via the communication unit, medical examination data from a medical examination instrument which obtains the examination data from the body part.

According to an aspect of the present invention, there is provided a method for a self-examination comprising: obtaining medical examination guide information based on at least one of a symptom and a suspected disease, wherein the medical examination guide information includes information of a body part; displaying a patient image; displaying an icon for a self-examination on the patient image at a position corresponding to the body part; and receiving medical examination data from a medical examination instrument, wherein the medical examination instrument obtains the examination data from the body part.

According to another aspect of the present invention, there is provided a method for a self-examination comprising: outputting a survey about at least one of a symptom and a suspected disease; receiving a reply to the survey; obtaining medical examination guide information based on at least one of the symptom and the suspected disease, wherein the medical examination guide information includes information of a body part; displaying a patient image; displaying an icon for a self-examination on the patient image at a position corresponding to the body part; and receiving medical examination data from a medical examination instrument, wherein the medical examination instrument obtains the examination data from the body part.

According to another aspect of the present invention, there is provided a method for a self-examination comprising: capturing a patient image; storing the patient image; obtaining medical examination guide information based on at least one of a symptom and a suspected disease, wherein the medical examination guide information includes information of a body part; displaying a patient image; displaying an icon for a self-examination on the patient image at a position corresponding to the body part; receiving medical examination data from a medical examination instrument, wherein the medical examination instrument obtains the examination data from the body part; storing the patient image and the medical examination data; and transmitting at least a portion of the patient image and the medical examination data.

Advantageous Effects

The present invention has the following advantages.

According to exemplary embodiments of the present invention, a user can perform a self-examination (namely, he can do a medical examination himself) without help of a physician upon receiving medical examination guide information for the self-examination.

According to exemplary embodiments of the present invention, because a customized medical examination guide is performed according to a patient's symptom or suspected disease by an apparatus for the self-examination, the user can effectively examine his body.

According to exemplary embodiments of the present invention, because a manipulation method of medical examination instrument, precautions (i.e., matters that require attention), or the like, are provided by the apparatus for the self-examination to the user, the user can easily examine himself.

According to exemplary embodiments of the present invention, because a survey about a symptom or a suspected disease is posed by the apparatus for the self-examination to obtain accurate medical examination guide information, the user can accurately examine himself.

According to exemplary embodiments of the present invention, because the survey is posed or the user is informed to conduct self-examination at a point in time at which the self-examination is required, the user can timely examine himself.

According to exemplary embodiments of the present invention, because the results of the user's self-examination are transmitted by the apparatus for the self-examination to an external device, the doctor can determine the patient's disease with reference to the received self-examination results.

According to exemplary embodiments of the present invention, because the patient transmits also the process of performing the self-examination, the doctor can more clearly check the medical examination results.

According to exemplary embodiments of the present invention, because the doctor can receive the medical examination results in advance before a face-to-face treatment (i.e., clinic-based consultation) or a telemedicine (i.e., tele-consultation), time and cost required and incurred for a medical treatment can be reduced.

DESCRIPTION OF DRAWINGS

FIG. 15 is a view illustrating the output unit outputting a survey about a symptom in the self-examination according to the second exemplary embodiment of the present invention.

FIG. 16 is a view illustrating the output unit outputting a survey about a suspected disease.

MODE FOR INVENTION

Figure 1:
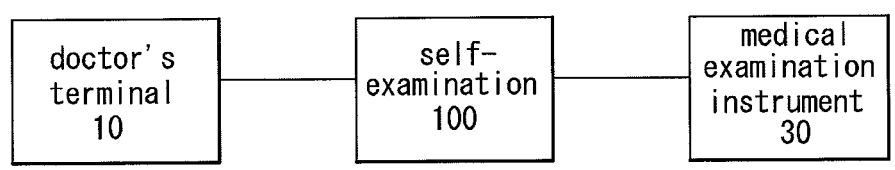
FIG. 1 is a view illustrating telemedicine according to an exemplary embodiment of the present invention.

The terminology used herein is for the purpose of describing particular embodiments only and is not intended to be limiting of the invention.

The present invention may be embodied in many different forms and may have various embodiments, of which particular ones will be illustrated in drawings and will be described in detail. However, it should be understood that the following exemplifying description of the invention is not meant to restrict the invention to specific forms of the present invention but rather the present invention is meant to cover all modifications, similarities and alternatives which are included in the spirit and scope of the present invention.

The same reference numerals will be used throughout to designate the same or like components, and a repeated description may be omitted.

The present invention is not limited to the exemplary embodiments described hereinafter.

Exemplary embodiments of the present invention will now be described with reference to the accompanying drawings.

An apparatus for a self-examination 100 according to an exemplary embodiment will now be described with reference to FIG. 1. FIG. 1 is a view illustrating telemedicine according to an exemplary embodiment of the present invention.

The apparatus for the self-examination 100 may be equipment for providing medical examination guide information for the self-examination. The self-examination refers to performing medical examination by a patient himself, rather than by physicians (or medical personnel) including a doctor, a nurse, and so on. In general, a medical examination may typically performed such that when a patient see a doctor, the doctor recognizes basic symptoms of the patient through questions and then examines the patient by using a medical examination instrument 30 such as a stethoscope, a thermometer, or the like. In contrast, when the doctor is not able to directly examine the patient, the patient may perform the examination process, which is to be performed by a physician, on himself by himself.

For example, as shown in FIG. 1, when the patient and a physician perform telemedicine or remote image medical treatment through a communication network at mutually remote areas, because a doctor or a nurse cannot examine the patient, the patient may examine himself. In another example, in the telemedicine, the patient may perform a simple self-examination before consulting with the doctor and provide the results to the doctor, to thus effectively perform a medical treatment in terms of time and cost. In another example, patients of chronic illness, such as a diabetic, a patient of metabolic syndrome, a hypertensive, and so on, periodically undergo the same checkup repeatedly. In this case, it may be advantageous for the patient to examine himself and transfer the results to a hospital (or a doctor), rather than visiting the doctor to have a checkup each time inconveniently.

Namely, the self-examination may refer to a patient's behavior of directly performing the entirety or a portion of the process of examining the patient by a physician. Here, the physician may have a broad concept including a medical assistant, a health manager, a hospital, a pharmacy, a pharmacist, a medical adviser, a veterinarian, and the like, as well as a doctor or a nurse, and the patient may be construed to designate targets of a medical service, rather than a person who is suffering a disease or an illness. Also, the patient is not necessarily limited to human beings but may include any life who can be provided with a medical service.

In order to perform medical examination, there may be a case in which a high level of special medical knowledge is required, or in order to handle the medical examination instrument 30 for performing such a medical examination, relevant basic knowledge may be required, so the patient may have difficulty in performing the self-examination by himself without any help. Thus, in order to solve such a problem, the apparatus for the self-examination 100 provides medical examination guide information to the patient to allow the patient to easily perform the self-examination.

Figure 2:
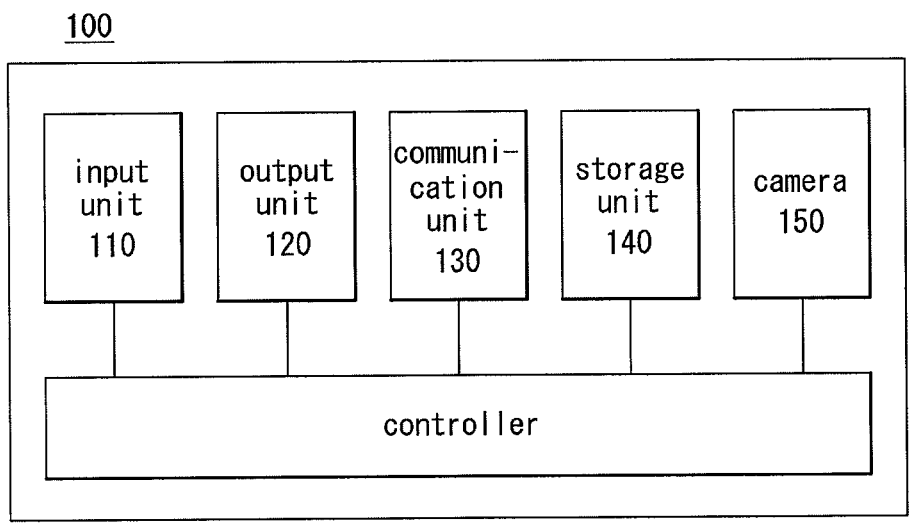
FIG. 2 is a schematic block diagram of an apparatus for a self-examination according to an exemplary embodiment of the present invention.

The configuration of the apparatus for the self-examination 100 according to an exemplary embodiment of the present invention will now be described with reference to FIGS. 2 and 3. FIG. 2 is a schematic block diagram of an apparatus for the self-examination 100 according to an exemplary embodiment of the present invention, and FIG. 3 is a perspective view of the apparatus for the self-examination 100 according to an exemplary embodiment of the present invention.

Figure 3:
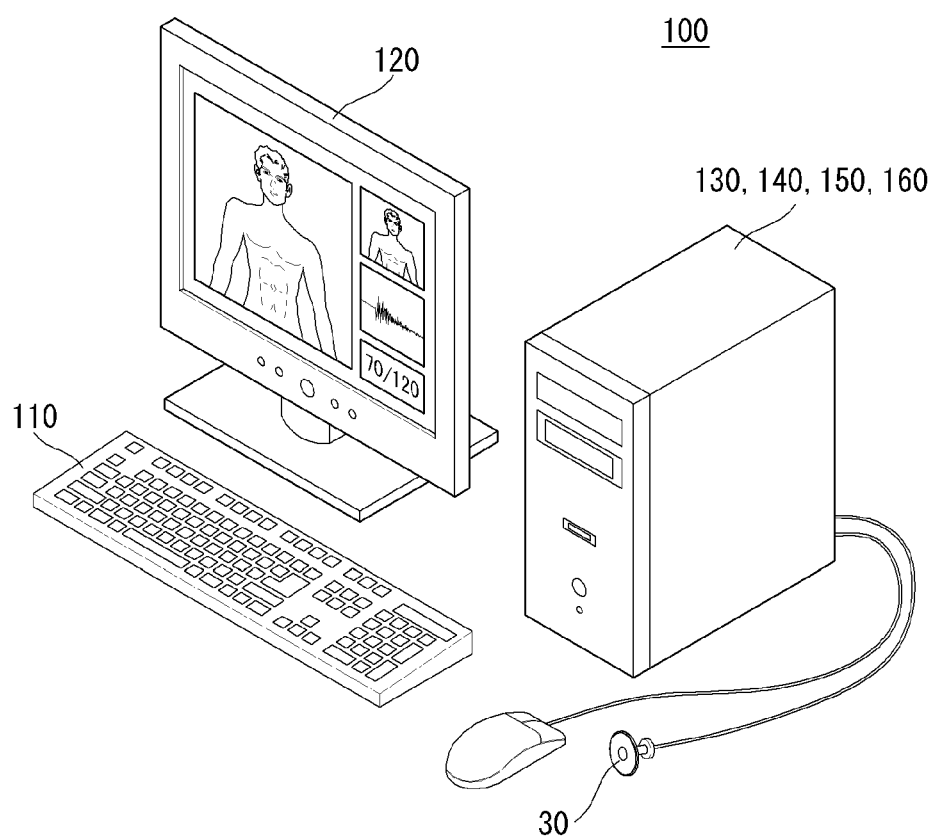
FIG. 3 is a perspective view of the apparatus for the self-examination according to an exemplary embodiment of the present invention.

As shown in FIGS. 2 and 3, the apparatus for the self-examination 100 for guiding the self-examination may include at least one of an input unit 110 for receiving information from a user, an output unit 120 for outputting information, a communication unit 130 for communicating with an external device, a storage unit 140 for storing information, a camera 150 for capturing a patient image, and a controller 160 for obtaining medical examination guide information and controlling the other elements of the apparatus for the self-examination 100. Hereinafter, the elements of the apparatus for the self-examination 100 will now be described.

The input unit 110 may receive information from a user. The input unit 110 may receive information in various manners. The input unit 110 may include at least one of a keyboard, a mouse, a touch screen, and a microphone. The input unit 110 may receive information from a user. For example, the input unit 110 may receive information regarding symptoms or information regarding health from the user.

The output unit 120 may output information. The user may be provided with information through the output unit 120. The output unit 120 may output information in various manners. The output unit 120 may output the information by using a visual signal, an audible signal, and a tactile (or haptic) signal. The output unit 120 may include a display, a speaker, a vibrator, and the like. The output unit 120 may output, for example, medical examination guide information to allow the user to perform the self-examination.

The communication unit 130 may communicate with an external device. Here, the external device may include a medical server 20, a doctor's terminal, a pharmacist's terminal, a personal computer, a mobile communication terminal, and the like. Also, the external device may include the medical examination instrument 30. For example, the communication unit 130 may receive medical examination data from the medical examination instrument 30. In detail, the communication unit 130 may receive an auscultation sound obtained by auscultating the patient from an electronic stethoscope. In another example, the communication unit 130 may transmit such medical examination data to the medical server 20, the doctor's terminal 10, or the like. Here, the communication unit 130 may be configured as a single module physically. Also, the communication unit 130 may include a plurality of modules physically.

The communication unit 130 may perform wireline communication or wireless communication through wired/wireless network. For example, the communication unit 130 may perform wireline communication such as a universal serial bus (USB), an RS-232 scheme, and the like. In another example, the communication unit 130 may perform wireless communication such as Wi-Fi, WiBro, Bluetooth™, ZigBee™, RFID, IrDA, and the like. The method according to which the communication unit 130 performs communication is not limited to the foregoing examples but may include various other methods of transmitting and receiving information to and from the external device.

The storage unit 140 may store information. The storage unit 140 may store various kinds of information for the self-examination. The storage unit 140 may store personal information regarding the user, i.e., the patient. The personal information may include various kinds of information such as name, gender, age, height, weight, blood pressure, blood sugar level, medical history, and the like. The storage unit 140 may store various kinds of information for a survey about symptoms. Also, the storage unit 140 may store the patient image captured by the camera 150 (to be described) or medical examination data obtained by the medical examination instrument 30. The various types of information may be input through the input unit 110, received from the communication unit 130, or generated by the controller 160.

The storage unit 140 may include various storage mediums. For example, the storage unit 140 may include a flash memory, a RAM, a ROM, a hard disk, an SD card, an optical disk such as a CD or a Blu-ray disk, and the like. The storage unit 140 may be installed within the apparatus for the self-examination 100 or may be configured to be detachably mounted in the apparatus for the self-examination 100.

The camera 150 may capture an image. The camera 150 may capture a patient image. The camera 150 may capture a video or a still image. The image captured by the camera 150 may be output through the output unit 120 or stored in the storage unit 140. Also, the controller 160 may edit the image captured by the camera 150 and the storage unit 140 may store the edited image.

The controller 160 may obtain medical examination guide information and control the other elements of the apparatus for the self-examination 100. Here, the medical examination guide information may be information allowing the user to perform the self-examination. The medical examination guide information may include information regarding the order of medical examination, a body part to be examined, medical examination instrument to be used for the corresponding part, and the like. Details of the medical examination guide information will be described in explaining a medical examination guide method (to be described). The controller 160 may obtain such medical examination guide information and provide the same through the output unit 120 to the user to allow the user to perform the self-examination. Besides, the controller 160 may control various configurations of a medical examination guide device. Details of the controller 160 will be described in explaining the medical examination guide method (to be described).

A method for the self-examination according to an exemplary embodiment will now be described.

The method for the self-examination according to an exemplary embodiment will be described by using the apparatus for the self-examination 100. Here, the apparatus for the self-examination 100 is used to easily describe the method for the self-examination. Thus, the method for the self-examination according to an exemplary embodiment of the present invention is not limited to the apparatus for the self-examination 100 according to an exemplary embodiment of the present invention.

The method for the self-examination according to an exemplary embodiment of the present invention may be performed by using a different apparatus which performs the same function as that of the apparatus for the self-examination 100.

Figure 4:
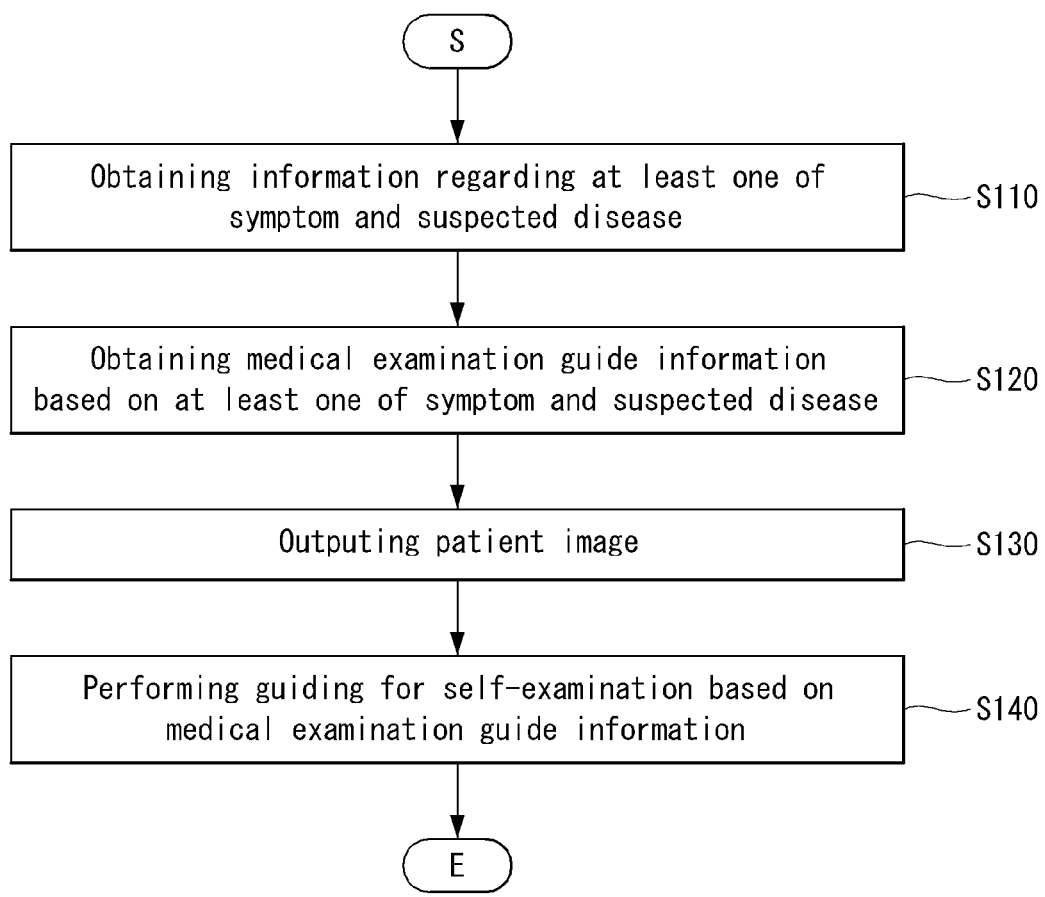
FIG. 4 is a flow chart illustrating the process of a method for the self-examination according to a first exemplary embodiment of the present invention.
Figure 5:
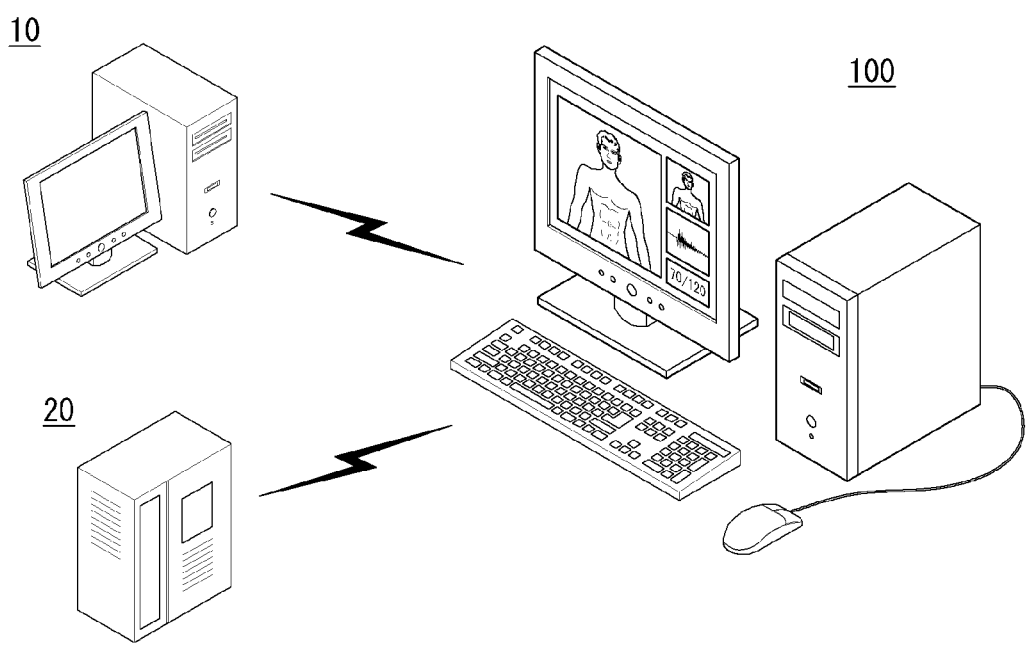
FIG. 5 is a view illustrating a method for receiving information regarding at least one of a symptom and a suspected disease from an external device in the method for the self-examination according to the first exemplary embodiment of the present invention.
Figure 6:
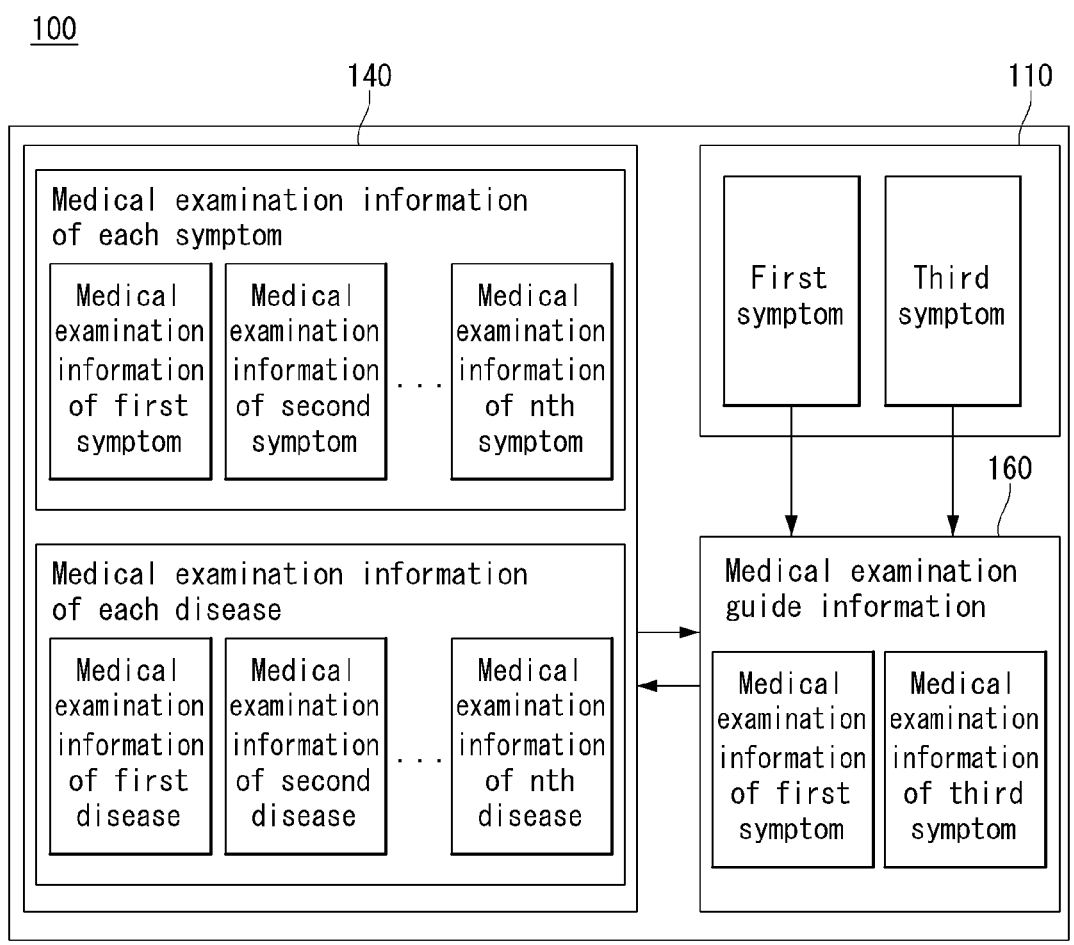
FIG. 6 is a view illustrating a method for obtaining medical examination guide information in the method for the self-examination according to the first exemplary embodiment of the present invention.

The method for the self-examination according to a first exemplary embodiment of the present invention will now be described with reference to FIGS. 4, 5, and 6. FIG. 4 is a flow chart illustrating the process of a method for the self-examination according to a first exemplary embodiment of the present invention. FIG. 5 is a view illustrating a method for receiving information regarding at least one of a symptom and a suspected disease from an external device in the method for the self-examination according to the first exemplary embodiment of the present invention. FIG. 6 is a view illustrating a method for obtaining medical examination guide information in the method for the self-examination according to the first exemplary embodiment of the present invention.

The method for the self-examination according to a first exemplary embodiment of the present invention may include at least one of step (S110) of obtaining information regarding at least one of a symptom and a suspected disease, step (S120) of obtaining medical examination guide information based on at least one of the symptom and the suspected disease, step (S130) of outputting a patient image, and step (S140) of guiding the self-examination based on the medical examination guide information. Hereinafter, the respective steps of the method for the self-examination according to the first exemplary embodiment of the present invention will be described.

The apparatus for the self-examination 100 may obtain information regarding at least one of a symptom and a suspected disease (S110).

The controller 160 may obtain information regarding at least one of a symptom and a suspected disease. Here, the symptom may refer to various symptoms, states, or the like, appearing when a person is ill. Also, the suspected disease may refer to a disease from which the person is suspected to be suffering as determined based on apparent symptoms. The controller 160 may obtain the information regarding such symptoms and suspected disease in various manners. The controller 160 may obtain information regarding at least one of the symptom and the suspected disease from, for example, the communication unit 130, the storage unit 140, and the input unit 110. Hereinafter, a detailed method for obtaining information regarding at least one of the symptom and the suspected disease by the apparatus for the self-examination 100 will now be described.

First, the controller 160 may obtain information regarding at least one of the symptom and the suspected disease through the communication unit 130. As shown in FIG. 5, the communication unit 130 may receive information regarding at least one of the symptom and the suspected disease from an external device, and the controller 160 may obtain such information through the communication unit 130.

For example, the apparatus for the self-examination 100 may perform telemedicine through communication with the doctor's terminal 10. Here, the apparatus for the self-examination 100 may transmit the patient image and the doctor's terminal 10 may transmit an image of the doctor to allow a medical image treatment between the patient and the doctor. Accordingly, the doctor may ask questions about his condition to recognize a symptom and input the results to the doctor's terminal 10. The communication unit 130 of the apparatus for the self-examination 100 may receive the information regarding the symptom input by the doctor from the doctor's terminal 10, and the controller 160 may obtain the information regarding the symptom from the communication unit 130.

In another example, in telemedicine using the apparatus for the self-examination 100 and the doctor's terminal 10, the doctor may ask questions about his condition and estimate a disease of the patient according to answers based on a medical knowledge. The doctor may input such a suspected disease to the doctor's terminal 10, and the communication unit 130 of the apparatus for the self-examination 100 may receive the information regarding the suspected disease from the doctor's terminal 10. Accordingly, the controller 160 may receive the information regarding the suspected disease from the communication unit 130.

In another example, the apparatus for the self-examination 100 may receive information regarding a symptom from the patient and transmit such a symptom to the medical sever 20. The medical server 20 may manage general information regarding physical conditions of the patient. The medical server 20 may be a server managing general information regarding the physical conditions of the patient. The medical server 20 may manage information regarding body conditions such as age, gender, height, weight, and the like, diet information such as a caloric intake, or the like, exercise information such as an exercise time, or the like. The medical server 20 may receive information regarding the symptoms of the patient from the apparatus for the self-examination 100, and determine a suspected disease in consideration of the information regarding the patient collectively. The communication unit 130 may receive information regarding the determined suspected disease from the medical server 20, and accordingly, the controller 160 may obtain the information regarding the suspected disease.

Or, the controller 160 may obtain information regarding at least one of the symptom and the suspected disease from the storage unit 140.

For example, the storage unit 140 may store information regarding at least one of the symptom and the suspected disease of the patient. The controller 160 may obtain the information regarding at least one of the symptom and the suspected disease from the storage unit 140. When the apparatus for the self-examination 100 regularly performs the self-examination, the storage unit 140 may store information regarding at least one of the symptom and the suspected disease of the patient who performs the self-examination. In detail, when the patient is a patient of a chronic disease, the patient needs to be examined periodically. Thus, the storage unit 140 may store information regarding the patient of chronic disease.

In another example, the storage unit 140 may store information regarding at least one of symptoms and suspected diseases of a plurality of patients. The input unit 110 may receive patient identification information from the user. Such information may be the name of the patient, a patient number, or the like. The controller 160 may select information regarding at least one of a symptom and a suspected disease corresponding to patient identification information among the information regarding the at least of the symptoms and suspected diseases of the plurality of patients stored in the storage unit 140. Accordingly, the controller 160 can obtain the information regarding at least one of the symptom and the suspected disease from the storage unit 140.

Or, the controller 160 may obtain information regarding at least one of the symptom and the suspected disease through the input unit 110.

For example, the input unit 110 may receive information reflecting a suspected disease from the user, and the controller 160 may obtain information regarding a suspected disease according to the received information.

In another example, the output unit 120 may output a symptom survey, the input unit 110 may receive a reply to the symptom survey, and the controller 160 may obtain information regarding the symptom according to the reply. Details of the method for obtaining information regarding a symptom through the symptom survey will be described in detail in explaining a method for the self-examination according to a second exemplary embodiment of the present invention.

Or, the controller 160 may generate information regarding a suspected disease by using information regarding a symptom. For example, as described above, the controller 160 may obtain information regarding a symptom through at least one of the communication unit 130, the storage unit 140, and the input unit 110. The controller 160 may determine a suspected disease based on the obtained information regarding the symptom. Accordingly, the controller 160 can obtain the information regarding a suspected disease.

The apparatus for the self-examination 100 may obtain medical examination guide information based on at least one of the symptom and the suspected disease (S120).

As described above, the controller 160 may obtain the medical examination guide information based on at least one of the symptom and the suspected disease obtained through various methods. Here, the medical examination guide information may refer to information for guiding the user to perform the self-examination. The medical examination guide information may include a position of a body part at which the self-examination is to be performed, the name of the body part, a type of the medical examination instrument 30 to be used for the self-examination, information for guiding manipulation of the medical examination instrument 30, precautions (i.e., matters that require attention) in the case of the self-examination, and the like. The controller 160 can obtain the medical examination guide information in various manners. Hereinafter, the method of obtaining the medical examination guide information in various manners will now be described.

As shown in FIG. 6, the storage unit 140 may store medical examination information of various symptoms. The controller 160 may obtain the information regarding symptoms as described above. The controller 160 may determine at least one of the plurality of medical examination information stored in the storage unit 140, as medical examination guide information by using the obtained information regarding the symptom. For example, the storage unit 140 may store first medical examination information regarding a first symptom, second medical examination information regarding a second symptom, and third medical examination information regarding a third symptom. When the controller 160 obtains information reflecting the first and third symptoms, it may determine the first and third medical examination information as medical examination guide information.

Similarly, the storage unit 140 may store medical examination information of various diseases. As described above, the controller 160 may obtain information regarding a suspected disease. The controller 160 may determine at least one medical examination information corresponding to the suspected disease, among the medical examination information of each disease, as medical examination guide information. For example, the storage unit 140 may store medical examination information regarding a head cold, medical examination information regarding a sore throat, medical examination information regarding enteritis, or the like. When the suspected disease is a cold, the controller 160 may determine the medical examination information regarding the head cold and the medical examination information regarding the sore throat corresponding to the cold as a suspected disease, as the medical examination guide information.

Or, the communication unit 130 of the apparatus for the 100 may transmit information regarding at least one of the symptom and the suspected disease obtained by the controller 160 to an external device, the external device generates medical examination guide information accordingly, and the apparatus for the self-examination 100 may obtain the medical examination guide information from the external device through the communication unit 130.

The apparatus for the self-examination 100 may output the patient image (S130).

The output unit 120 of the apparatus for the self-examination 100 may output the patient image. The patient image may include an actual image regarding the patient and a substitute image. Here, the actual image of the patient may refer to a video and a still image obtained by capturing an image of the patient. Meanwhile, the substitute image may refer to an image of the patient using an avatar, a character, a model, and the like, rather than an actual image of the patient. Here, the camera 150 may capture an image of the patient obtain the patient image, and the controller 160 may obtain the patient image from the camera 150, and the output unit 120 may output the patient image under the control of the controller 160.

The apparatus for the self-examination 100 may guide for the self-examination based on medical examination guide information (S140).

The apparatus for the self-examination 100 may guide the self-examination of the patient according to a method such as displaying a body part on the patient image, outputting a message informing about the type of a medical examination instrument, or the like, through the output unit 120. The output unit 120 may guide the self-examination in various manners.

Figure 7:
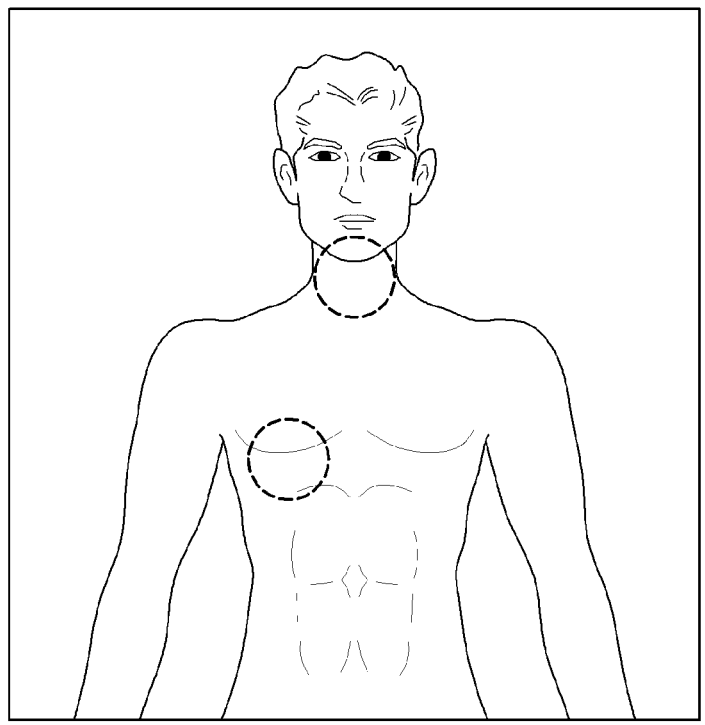
FIG. 7 is a view illustrating an output unit displaying a body part in the method for the self-examination according to the first exemplary embodiment of the present invention.
Figure 8:
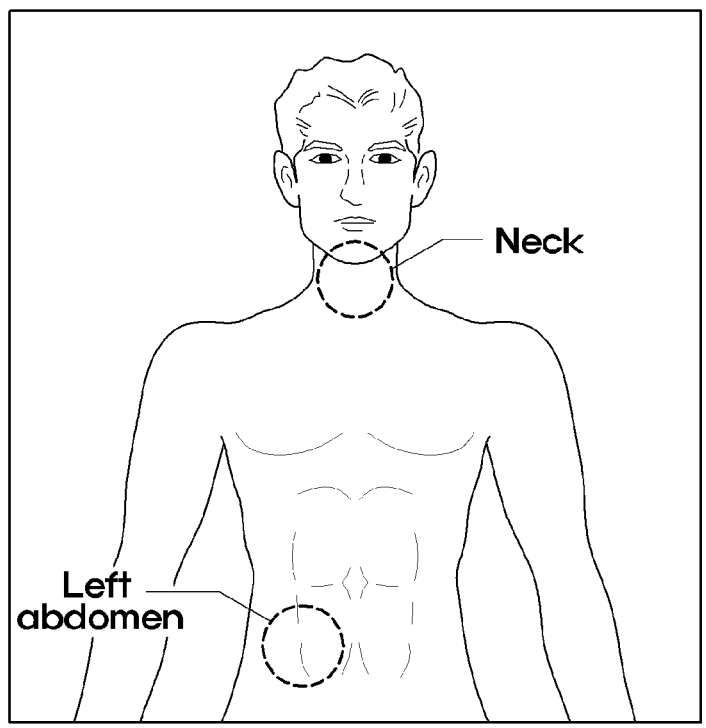
FIG. 8 is a view illustrating the output unit outputting the names of body parts in the method for the self-examination according to the first exemplary embodiment of the present invention.
Figure 9:
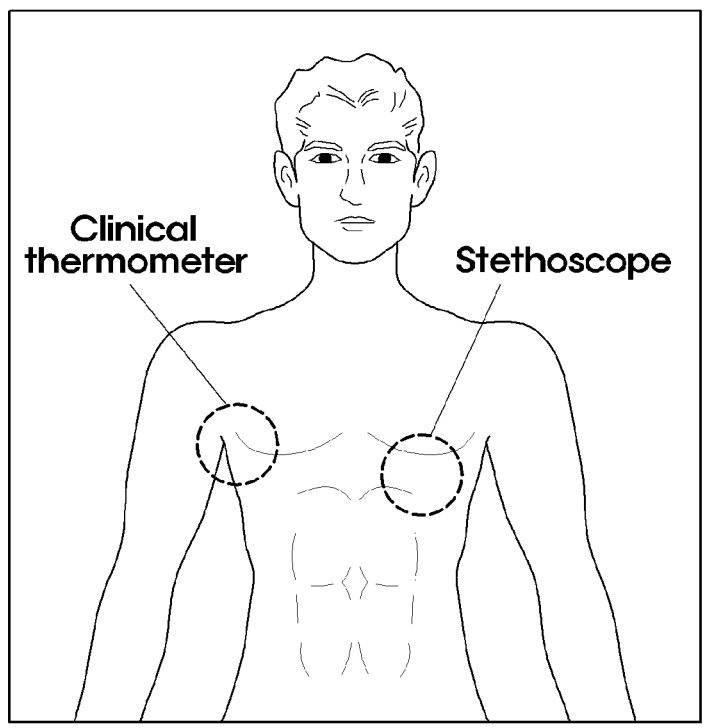
FIG. 9 is a view illustrating the output unit outputting types of medical examination instruments in the method for the self-examination according to the first exemplary embodiment of the present invention.
Figure 10:
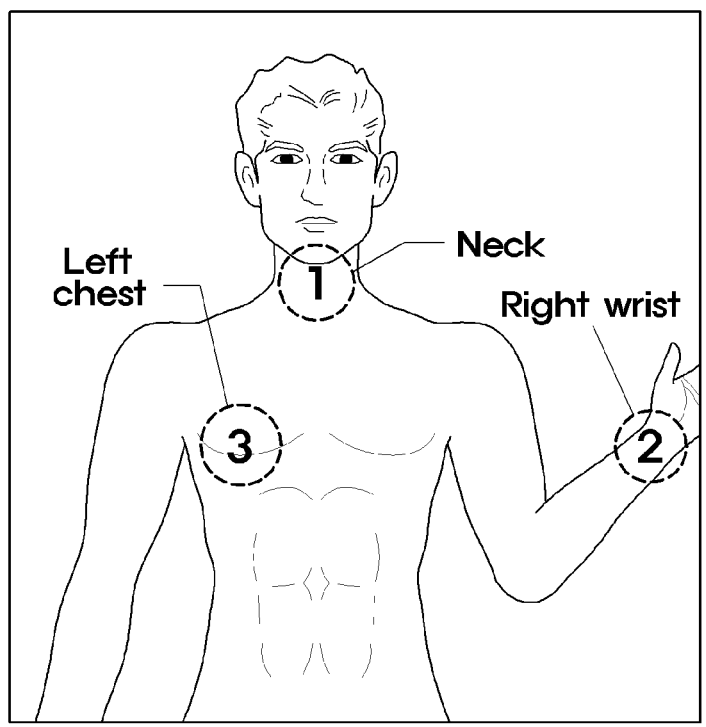
FIG. 10 is a view illustrating the output unit outputting the examination order in the method for the self-examination according to the first exemplary embodiment of the present invention.
Figure 11:
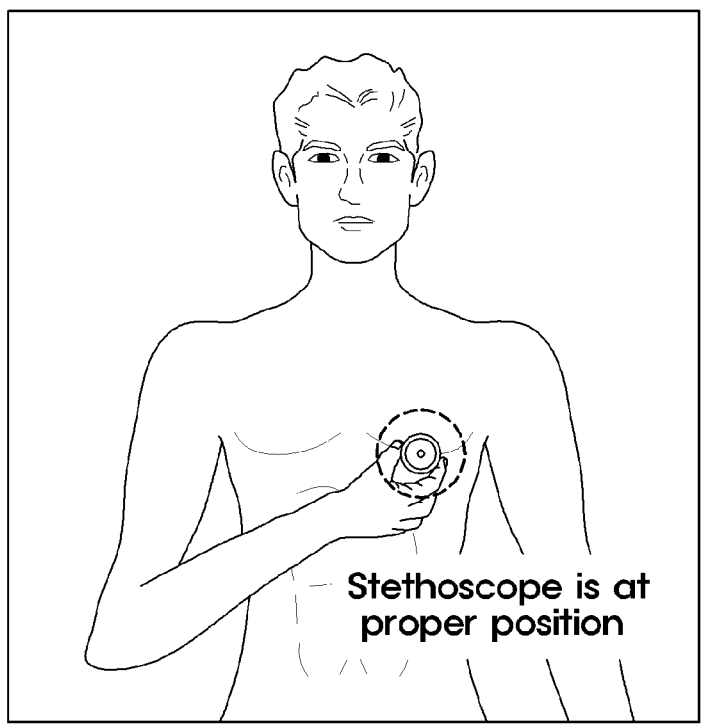
FIG. 11 is a first view illustrating the output unit outputting a message instructing a manipulation of a medical examination instrument in the method for the self-examination according to the first exemplary embodiment of the present invention.
Figure 12:
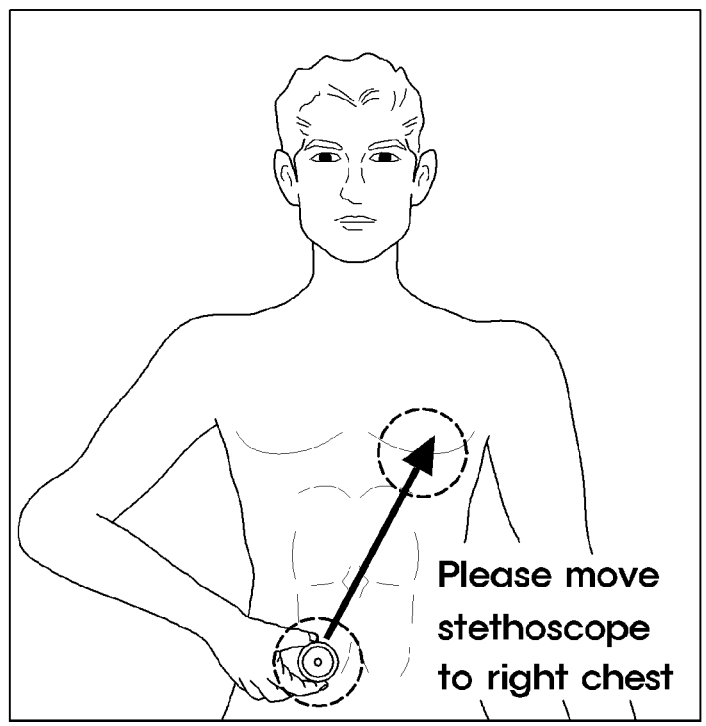
FIG. 12 is a second view illustrating the output unit outputting a message instructing a manipulation of a medical examination instrument in the method for the self-examination according to the first exemplary embodiment of the present invention.
Figure 13:
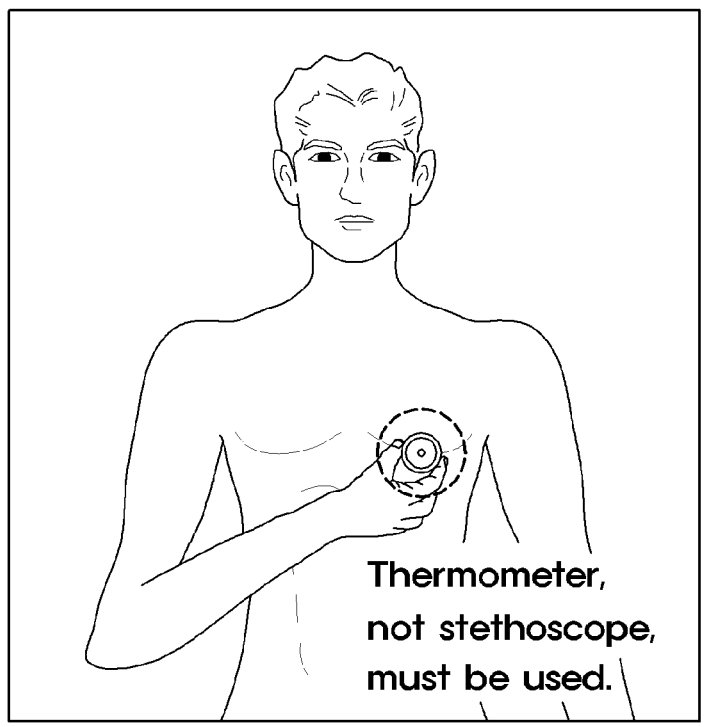
FIG. 13 is a view illustrating the output unit outputting a message regarding a type of a medical examination instrument in the method for the self-examination according to the first exemplary embodiment of the present invention.

Hereinafter, the method of guiding the self-examination based on the medical examination guide information by the apparatus for the self-examination 100 will now be described with reference to FIGS. 7, 8, 9, 10, 11, 12, and 13. FIG. 7 is a view illustrating the output unit 120 displaying a body part in the method for the self-examination according to the first exemplary embodiment of the present invention. FIG. 8 is a view illustrating the output unit 120 outputting the names of body parts in the method for the self-examination according to the first exemplary embodiment of the present invention. FIG. 9 is a view illustrating the output unit 120 outputting types of medical examination instruments 30 in the method for the self-examination according to the first exemplary embodiment of the present invention. FIG. 10 is a view illustrating the output unit 120 outputting the examination order in the method for the self-examination according to the first exemplary embodiment of the present invention. FIGS. 11 and 12 are views illustrating the output unit 120 outputting a message instructing a manipulation of the medical examination instrument 30 in the method for the self-examination according to the first exemplary embodiment of the present invention. FIG. 13 is a view illustrating the output unit 120 outputting a message regarding a type of a medical examination instrument 30 in the method for the self-examination according to the first exemplary embodiment of the present invention.

As shown in FIG. 7, the output unit 120 may display an icon for the self-examination, a position corresponding to a body part which is to be examined on the patient image based on the medical examination guide information. Here, the medical examination guide information may include information regarding the body part. The controller 160 may determine the position corresponding to the body part on the patient image based on the information regarding the body part. For example, the controller 160 may determine the position corresponding to the body part on the patient image according to a color pattern, a shape pattern, or the like. In another example, the controller 160 may determine the position corresponding to the body part on the patient image by using an augmented reality scheme. The controller 160 may output the icon indicating the body part which is to be examined at the determined position. Accordingly, the user can recognize the body part and perform the self-examination.

Or, as shown in FIG. 8, the output unit 120 may output the name of the body part based on the medical examination guide information. Here, the medical examination guide information may include information regarding the name of the body part. The controller 160 may control the output unit 120 to output the name of the body part based on the medical examination guide information. Here, the patient image may be an image obtained by making actual images obtained by capturing the patient image symmetrical horizontally. Accordingly, the user can intuitionally recognize the position of his body upon viewing the patient image.

Or, as shown in FIG. 9, the output unit 120 may output the types of medical examination instruments 30 based on the medical examination guide information. Here, the medical examination guide information may include information regarding types of the medical examination instruments 30. The controller 160 may display the types of the medical examination instruments 30 on the display or output the same as a voice message through a speaker based on the medical examination guide information.

Or, as shown in FIG. 10, the output unit 120 may output the medical examination order based on the medical examination guide information. Here, the medical examination guide information may include information regarding a plurality of body parts and information regarding the medical examination order of each of the plurality of body parts. For example, when the medical examination guide information reflects neck as a first body part, right wrist as a second body part, and a left chest as a third body part, the controller 160 may indicate the medical examination order on the neck, right wrist, and left chest as shown in FIG. 10.

Or, the output unit 120 may output a suspected disease. When the controller 160 obtains the suspected disease, the controller 160 may control the output unit 120 to output the suspected disease. For example, the input unit 110 obtains a symptom, the controller 160 determines a suspected disease based on the symptom, and the output unit 120 may output the suspected disease. In detail, the input unit 110 may receive symptoms that the user has a sore throat and a fever from the user, the controller 160 may determine a cold as a suspected disease, and the output unit 120 may output a message for the self-examination with respect to the cold.

Or, the output unit 120 may output a message indicating a manipulation of the medical examination instrument 30 based on relative positions of the medical examination instrument 30 and the body part. Here, the controller 160 may obtain the position of the medical examination instrument 30 through the communication unit 130 or the camera 150, and control the output unit 120 to output a message indicating a manipulation of the medical examination instrument 30 based on the relative positions of the medical examination instrument 30 and the body part.

For example, as shown in FIG. 11, when the medical examination instrument 30 is at the same position as that of the body part, the controller 160 may control the output unit 120 to output a message reflecting that the medical examination instrument 30 is at the body part. Or, the controller 160 may control the output unit 120 to simply output an alarm message of a voice or an image informing the user accordingly.

In another example, when the medical examination instrument 30 is at a position different from the body part, the controller 160 may control the output unit 120 to output a message reflecting information that the position of the medical examination instrument 30 is wrong. Or, the controller 160 may control the output unit 120 to output a message indicating a manipulation of the medical examination instrument 30. Here, as shown in FIG. 12, the message indicating a manipulation of the medical examination instrument 30 may include a message or a mark indicating at least one of a direction and a distance in which and along which the medical examination instrument 30 needs to be moved to be positioned at the body part.

Or, the output unit 120 may output a message indicating whether or not the type of the medical examination instrument 30 is proper. The controller 160 may obtain the type of medical examination instrument used for an actual medical examination through the communication unit 130 or the camera 150. Or, the controller 160 may obtain information regarding the type of the medical examination instrument 30 to be used for a medical examination based on the medical examination guide information. Here, the medical examination guide information may include information regarding the type of the medical examination instrument 30 for examining the body part. The controller 160 may compare the type of the medical examination instrument 30 according to the medical examination guide information and the type of the actually used medical examination instrument 30 and, when the two types are different, the controller 160 may control the output unit 120 to output a message indicating that a wrong medical examination instrument 30 is in use. For example, when the left chest needs to be examined with a thermometer but a stethoscope is in use, the controller 160 may control the output unit 120 to output a message indicating that the thermometer, not the stethoscope, needs to be used, as shown in FIG. 13.

Or, the output unit 120 may output a message regarding precautions (namely, matters that require attention) in medical examination. The controller 160 may control the output unit 120 to output a message regarding precautions in medical examination based on the medical examination guide information. For example, when the stethoscope is used and if the patient breathes out or breathes in, auscultation cannot be properly performed. The medical examination guide information may include such precautions. The controller 160 may control the output unit 120 to output respective precautions according to various medical examinations based on the medical examination guide information.

The method of the self-examination according to the first exemplary embodiment of the present invention has the effect that because the medical examination guide for the self-examination is provided by the apparatus for the self-examination, the user can perform the self-examination without help of a physician.

Also, because a customized medical examination guide is provided according to a symptom or a suspected disease of the patient by the apparatus for the self-examination, the user can effectively perform the self-examination on his body.

In addition, because the manipulation of the medical examination instrument or the precautions in the medical examination is provided by the apparatus for the self-examination, the user can easily perform the self-examination.

Figure 14:
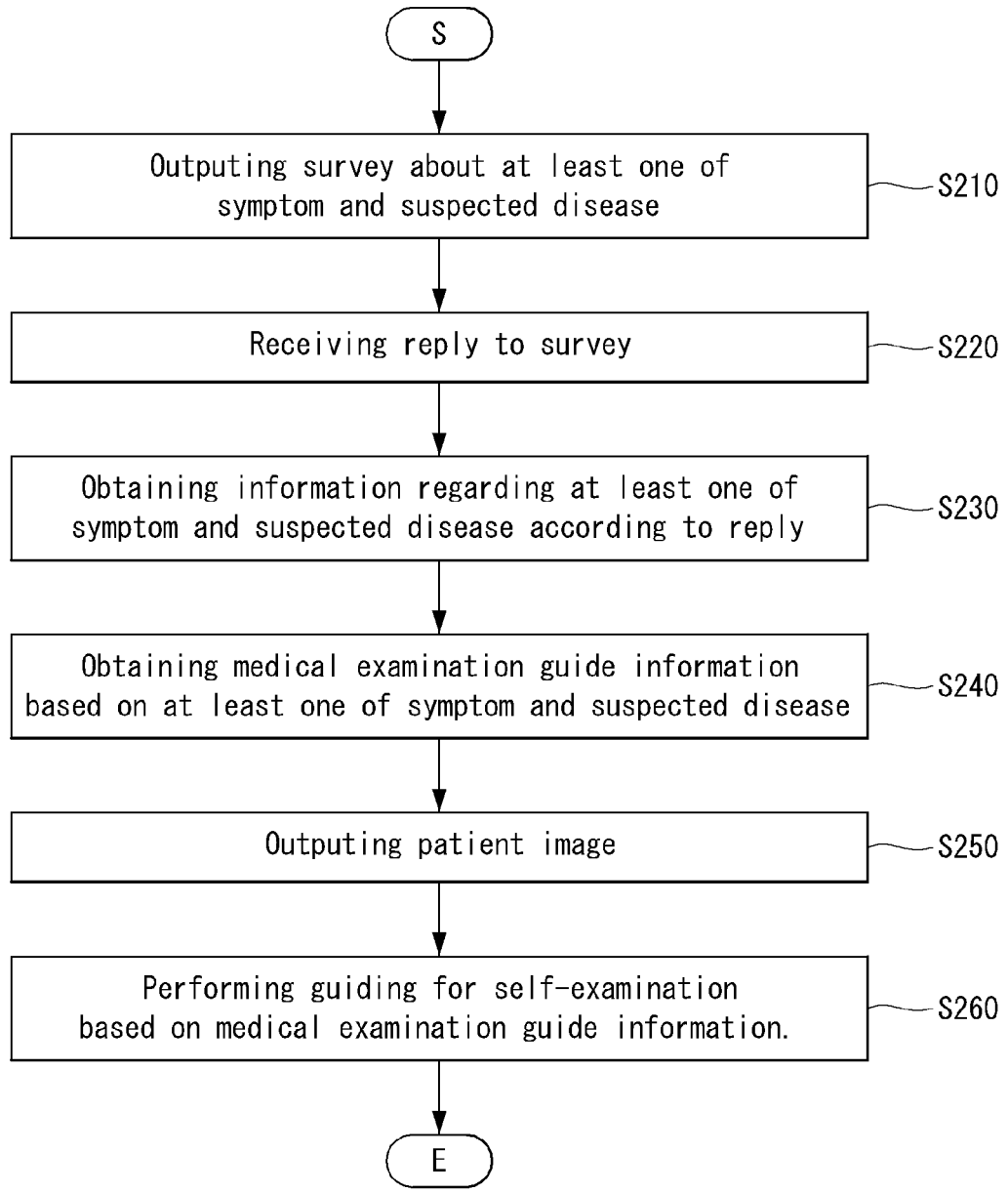
FIG. 14 is a flow chart illustrating the process of a method for the self-examination according to a second exemplary embodiment of the present invention.

A method for the self-examination according to a second exemplary embodiment of the present invention will now be described with reference FIGS. 14, 15, and 16. FIG. 14 is a flow chart illustrating the process of a method for the self-examination according to a second exemplary embodiment of the present invention. FIG. 15 is a view illustrating the output unit 120 outputting a survey about a symptom in the method for the self-examination according to the second exemplary embodiment of the present invention. FIG. 16 is a view illustrating the output unit 120 outputting a survey about a suspected disease.

The method for the self-examination according to the second exemplary embodiment of the present invention may include at least one of step (S210) of outputting a survey about at least one of a symptom and a suspected disease, step (S220) of receiving a reply to the survey, step (S230) of obtaining information regarding at least one of the symptom and the suspected disease according to the reply, step (S240) of obtain medical examination guide information based on at least one of the symptom and the suspected disease, step (S250) of outputting an patient image, and step (S260) of guiding the self-examination based on the medical examination guide information. Hereinafter, the respective steps of the method for the self-examination according to the second exemplary embodiment of the present invention will be described. Here, step (S230) of obtaining information regarding at least one of the symptom and the suspected disease according to the reply, step (S240) of obtain medical examination guide information based on at least one of the symptom and the suspected disease, step (S250) of outputting an patient image, and step (S260) of guiding the self-examination based on the medical examination guide information may be the same as content described above in describing the method for the self-examination according to the first exemplary embodiment of the present invention.

The apparatus for the self-examination 100 may output a survey about at least one of a symptom and a suspected disease (S210).

The storage unit 140 may store the survey about at least one of the symptom and the suspected disease. The controller 160 may control the output unit 120 to output the survey stored in the storage unit 140. The survey may include questions about the symptom, questions about the suspected disease, and questions about a body condition of the patient. For example, as shown in FIG. 15, the output unit 120 may output the survey about the symptom. In another example, as shown in FIG. 16, the output unit 120 may output the survey about the suspected disease. In another example, the output unit 120 may output questions about the patient's physical condition including name, age, gender, height, weight, blood pressure, blood sugar level, body temperature, and the like.

Here, the apparatus for the self-examination 100 may output such survey when predetermined conditions are met.

The controller 160 may control the output unit 120 to output the survey when a predetermined questionnaire time arrives according to a pre-set schedule. When the apparatus for the self-examination 100 performs the self-examination regularly at every certain period, it may output such survey regularly at every certain period. For example, when a physical examination (or a checkup) is performed regularly, the apparatus for the self-examination 100 may output the survey when a particular date arrives at the interval of one month. In another example, in case of a patient of a chronic disease, he needs to be regularly examines, so the controller 160 may questionnaire according to a predetermined medical examination schedule of the patient of chronic disease. The communication unit 130 may receive the schedule from an external device. Here, the external device may be the doctor's terminal 10, the medical server 20, or the like. Or, the schedule may be input to the input unit 110. Or, the storage unit 140 may store the schedule. The controller 160 may obtain the schedule from the input unit 110, the communication unit 130, and the storage unit 140, determine whether or not the questionnaire time has arrived, and output the survey when the questionnaire time arrives.

Or, the controller 160 may control the output unit 120 to output the survey when a pre-set time, which is ahead of a time reserved for a medical examination, arrives. In case of a pre-medical examination, the self-examination may be performed before the doctor's medical examination, and to this end, the controller 160 may questionnaire at the pre-set time, which is ahead of the time reserved for a medical examination.

For example, when the doctor's medical examination is reserved at 2:00 p.m., the controller 160 may control the output unit 120 to output the survey at 1:30 p.m., ahead of 2:00 p.m. Here, the communication unit 130 may obtain the time reserved for a medical examination from an external device. Or, the input unit 110 may receive the time reserved for a medical examination from the user. The controller 160 may output the survey based on the time reserved for a medical examination.

Or, the controller 160 may questionnaire when a signal reflecting abnormality in the user's physical condition from an external device. Here, the external device may be a health device detecting the user's physical condition. The health device may be, for example, a blood sugar sensor system, a blood pressure meter, a clinical thermometer, or the like. When the health device detects abnormality of user's biometric information, it may transmit a message indicating the abnormality to the apparatus for the self-examination, the communication unit 130 may receive the message, and the controller 160 may questionnaire when the signal is received.

Meanwhile, the apparatus for the self-examination may output a message indicating that a questionnaire time has arrived to the user, instead of outputting the survey or before outputting the survey. As described above, when the particular conditions are met, namely, when the questionnaire time according to the schedule arrives, or when it is a preset time ahead of the time reserved for a medical examination, or when abnormality of a biometric signal is detected, the apparatus for the self-examination may output a message indicating performing of the self-examination to the user. Or, the apparatus for the self-examination may transmit such a message to a mobile communication terminal of the user, so that the mobile communication terminal may output the message indicating the performing of the self-examination to the user.

Also, before questionnaring at least one of a symptom and a suspected disease, the apparatus for the self-examination may output a survey asking whether to questionnaire the symptom or whether to questionnaire the suspected disease. The output unit 120 may output a survey asking which of the symptom and the suspected disease is to be questionnaired, and the input unit 110 may receive a reply to the survey (S220). The controller 160 may questionnaire the symptom or the suspected disease based on the result of the reply.

The method for the self-examination according to the second exemplary embodiment of the present invention has the effect that because more accurate medical examination guide information is obtained by providing the survey about the symptom or the suspected disease by the apparatus for the self-examination, the user can perform more accurate self-examination. In addition, because the questions are provided or the user is informed to perform the self-examination at a point in time at which the self-examination is required, the user can timely perform the self-examination.

Figure 17:
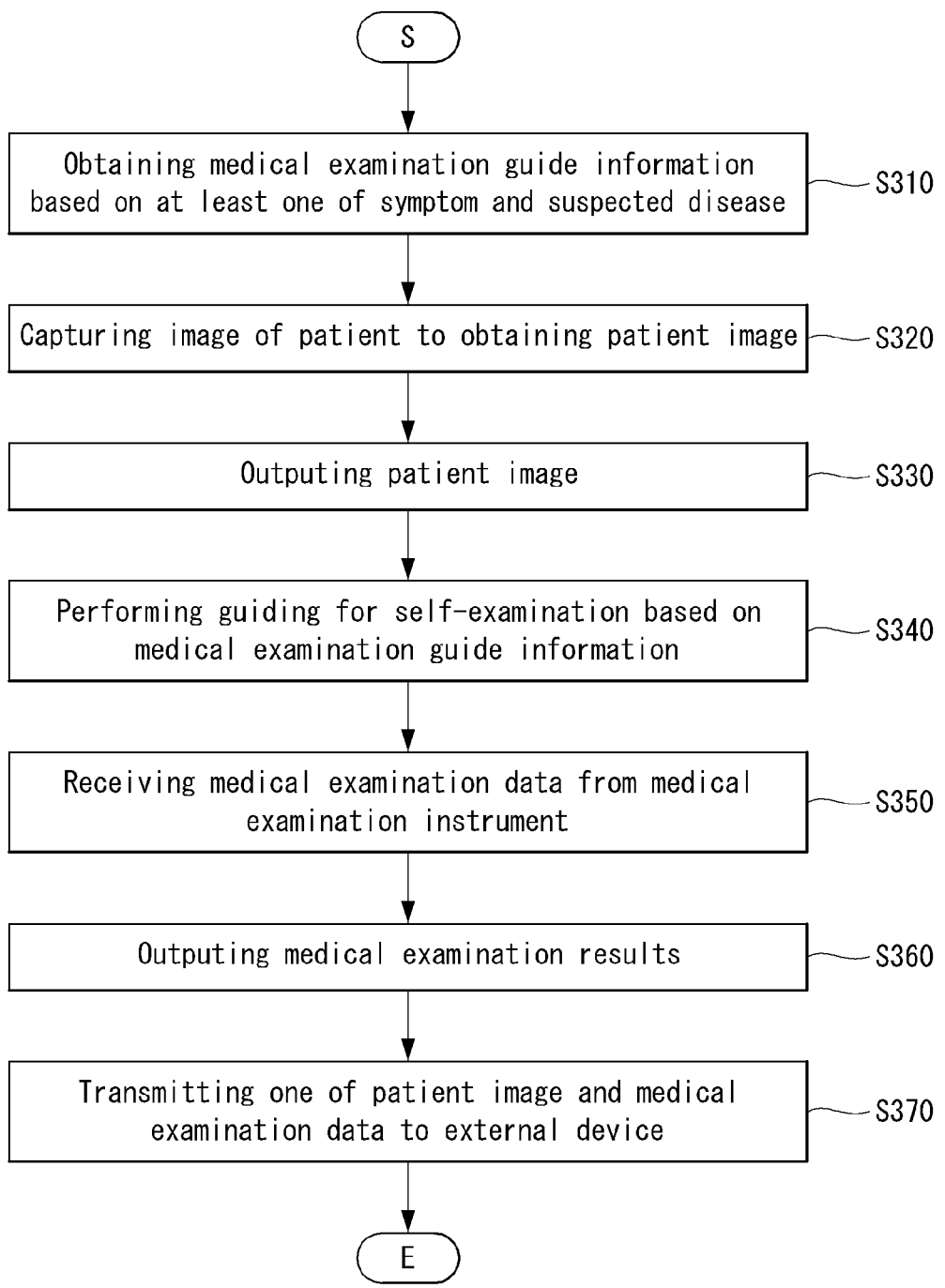
FIG. 17 is a flow chart illustrating the process of a method for the self-examination according to a third exemplary embodiment of the present invention.
Figure 18:
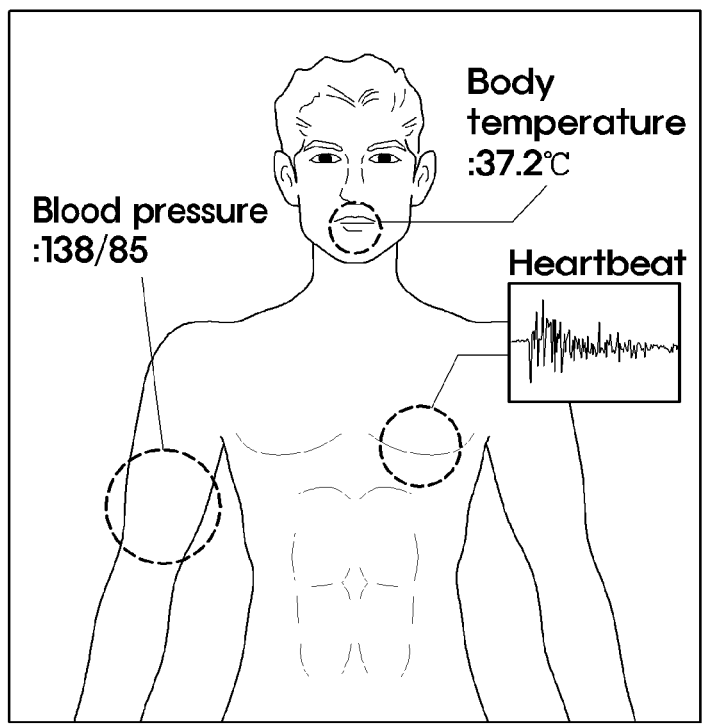
FIG. 18 is a first view illustrating the output unit outputting examination results in the method for the self-examination according to the third exemplary embodiment of the present invention.

A method for the self-examination according to a third exemplary embodiment of the present invention will now be described with reference FIGS. 17, 18, 19, 20, and 21. FIG. 17 is a flow chart illustrating the process of a method for the self-examination according to a third exemplary embodiment of the present invention. FIG. 18 is a first view illustrating the output unit 120 outputting examination results in the method for the self-examination according to the third exemplary embodiment of the present invention.

Figure 19:
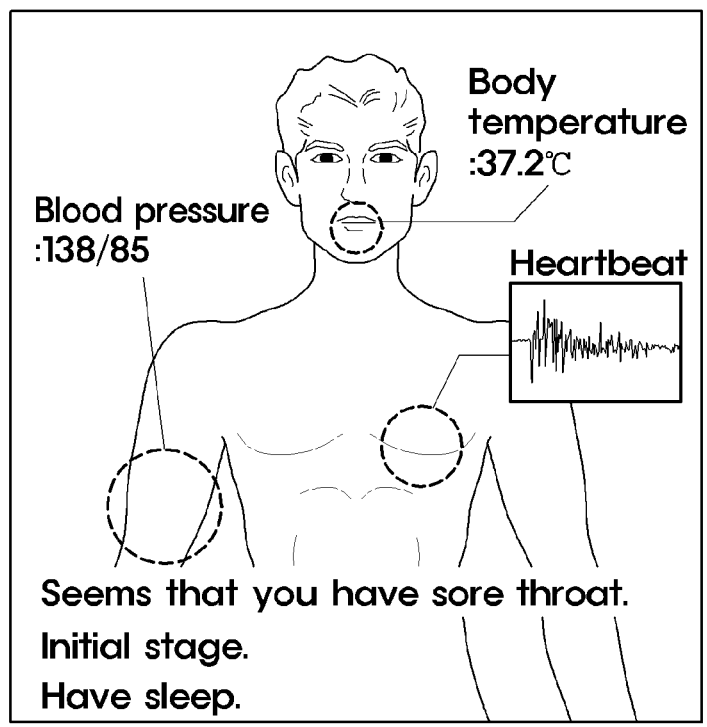
FIG. 19 is a second view illustrating the output unit outputting examination results in the method for the self-examination according to the third exemplary embodiment of the present invention.
Figure 20:
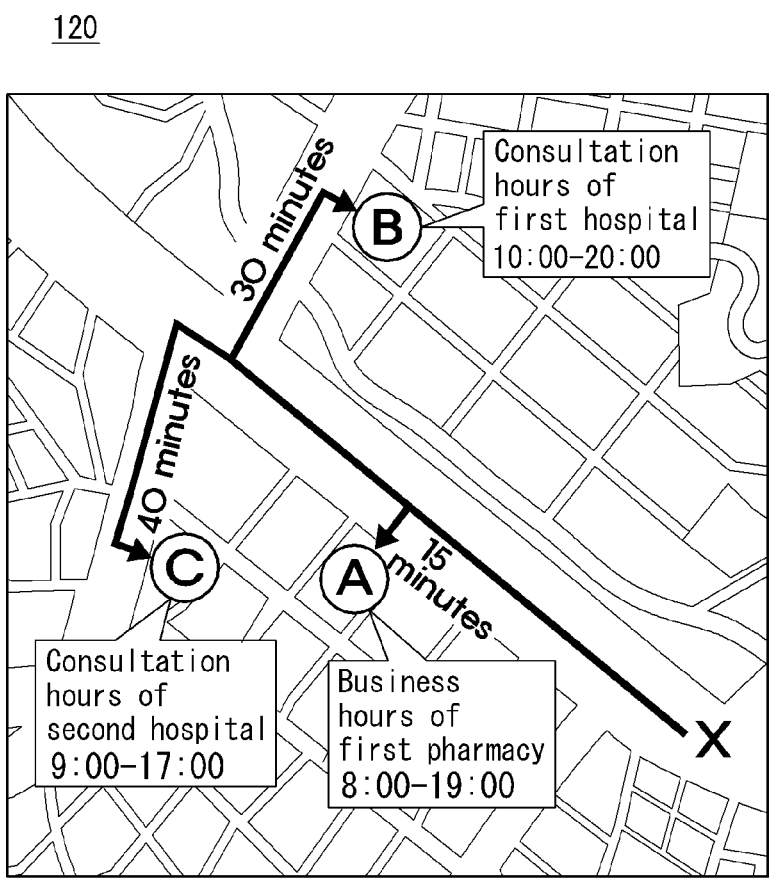
FIG. 20 is a third view illustrating the output unit outputting examination results in the method for the self-examination according to the third exemplary embodiment of the present invention.
Figure 21:
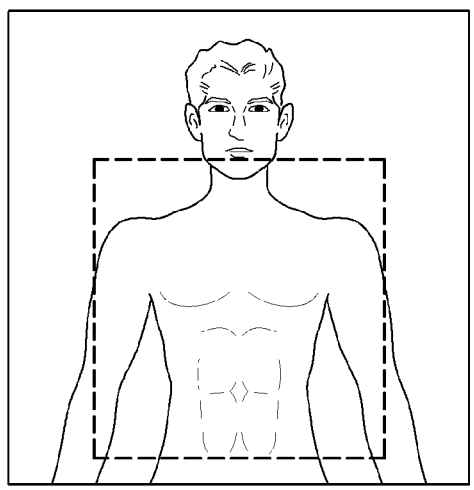
FIG. 21 is a view illustrating patient images transmitted to an external device in the method for the self-examination according to the third exemplary embodiment of the present invention.
Figure 21:
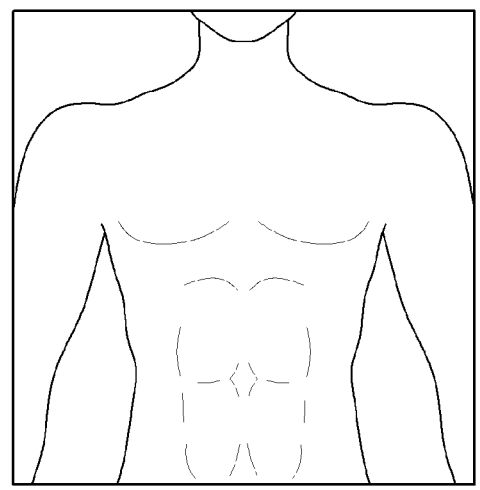

FIG. 19 is a second view illustrating the output unit 120 outputting examination results in the method for the self-examination according to the third exemplary embodiment of the present invention. FIG. 20 is a third view illustrating the output unit 120 outputting examination results in the method for the self-examination according to the third exemplary embodiment of the present invention. FIG. 21 is a view illustrating patient's images transmitted to an external device in the method for the self-examination according to the third exemplary embodiment of the present invention.

The method for the self-examination according to the third exemplary embodiment of the present invention may include at least one of step (S310) of obtaining medical examination guide information based on at least one of a symptom and a suspected disease, step (S320) of capturing an image of a patient, step (S330) of outputting the patient image, step (S340) of guiding the self-examination based on the medical examination guide information, step (S350) of receiving medical examination data from the medical examination instrument 30, step (S360) of outputting medical examination results, and step (S370) of transmitting at least one of the patient image and the medical examination data to an external device. Hereinafter, the respective steps of the method for the self-examination according to the third exemplary embodiment of the present invention will be described.

Here, step (S310) of obtaining medical examination guide information based on at least one of a symptom and a suspected disease and step (S340) of guiding the self-examination based on the medical examination guide information may be the same as content described above in describing the method for the self-examination according to the first and second exemplary embodiments of the present invention.

The apparatus for the self-examination 100 may capture an image of a patient (S320).

The camera 150 may capture an image of the patient to obtain the patient image. The patient image may include a real time image of the patient. Also, the patient image may include at least one of a video and a still image. The storage unit 140 may store the image captured by the camera 150. In this case, the controller 160 may edit the image captured by the camera 150 and the storage unit 150 may store the edited image.

The apparatus for the self-examination 100 may output the patient image (S330).

The output unit 120 may output the patient image captured by the camera 150. The controller 160 may control the output unit 120 to immediately output the image captured by the camera 150. Or, the controller 160 may control the output unit 120 to edit the image captured by the camera and output the same. For example, the controller 160 may control the output unit 120 to magnify the captured image and output the same. Accordingly, the user can be provided an accurate magnified image. In another example, the controller 160 may control the output unit 120 to reduce the image and output the same. In another example, the controller 160 may control the output unit 120 to output a horizontally symmetrical image. As the apparatus for the self-examination 100 outputs the horizontally symmetrical image, the user can more intuitively recognize the location of his body.

The apparatus for the self-examination 100 may obtain medical examination data from the medical examination instrument 30 (S350).

The communication unit 130 may receive the medical examination data from the medical examination instrument 30. Here, the medical examination instrument 30 may refer to an instrument for measuring medical examination data from a body part of the patient.

The medical examination instrument may include a thermometer, a stethoscope, a blood pressure meter, a blood glucose meter, an electrocardiograph, the camera 150, a body composition analyzer, a vascular screening system, an ultrasound image system, a urine test device, a pulsimeter, a blood collecting device, an X-ray device, an oxygen saturation test device, a dementia inspection system, a computerized axial tomography (CAT) device, a magnetic resonance imaging (MRI) device, an endoscope, a magnifier, a camera-integrated magnifier, and the like.

The medical examination instrument 30 can obtain biometric information from the patient. The user may directly manipulate the medical examination instrument 30 according to the self-examination guide to measure a body part. The medical examination instrument 30 may obtain medical examination data from the body part.

For example, the user may manipulate an electronic stethoscope to tightly attach it to his left chest, and the electronic stethoscope may measure an auscultation sound from the left chest and obtain a corresponding electronic signal. Here, the communication unit 130 may receive the electronic signal regarding the auscultation sound. Namely, the communication unit 130 may receive medical examination data regarding the body part from the medical examination instrument 30.

Here, the medical examination guide information may include information regarding the type of the medical examination instrument 30 used for examining the body part. In this case, when the type of the medical examination instrument 30 according to the medical examination guide information is different from the type of the medical examination instrument 30 manipulated by the user, the controller 160 may control the output unit 120 to output an error message indicating that a wrong medical examination instrument 30 is in use.

The apparatus for the self-examination 100 may output the medical examination results (S360).

The output unit 120 may output the medical examination results based on medical examination data. Here, the output unit 120 may output various medical examination results.

For example, as shown in FIG. 18, the output unit 120 may output the patient image and display the medical examination data at the portion corresponding to the body part on the patient image. The controller 160 obtains the medical examination data through the communication unit 130 and control the output unit 120 to display the medical examination data on the medical examination position based on the medical examination data.

In another example, as shown in FIG. 19, the output unit 120 may output the medical examination results including a presumed disease, the condition of the presumed disease, and corresponding advice. The controller 160 may obtain the medical examination data from the medical examination instrument 30 through the communication unit 130. The controller 160 may presume a disease the patient is suffering in consideration of the medical examination data, the symptoms, he suspected disease, and the like, and determine medical advice or a medical suggestion therefor. The controller 160 may control the output unit 120 to output the medical examination results.

In another example, as shown in FIG. 20, the output unit 120 may output information regarding a nearby hospital. The controller 160 may obtain information regarding the user's location. The information regarding the user's location can be obtained through a GPS technique by the communication unit 130. Or, the controller 160 may receive the location information through the input unit 110. Or, the location of the apparatus for the self-examination may be stored in the storage unit 140.

The controller 160 may search hospitals within a certain range based on the user's location. In detail, the controller 160 may obtain geographical information through the communication unit 130. Or, the controller 160 may use geographical information stored in the storage unit 140 or the like. The controller 160 may search hospitals within a certain range from the user's location based on the geographical information and the location information of the user. The controller 160 may control the output unit 120 to output information regarding at least one among searched hospitals. Here, the information regarding the hospital may include the location, name, phone number, doctor's name, business hours, time taken to reach, a path for a movement, and other supplementary information.

The apparatus for the self-examination may transmit at least one of the patient image and the medical examination data to an external device (S370).

The communication unit 130 may transmit the patient image to an external device. Also, the communication unit 130 may transmit the medical examination data to an external device. Here, the patient image may include images of the patient captured by the camera 150 during the medical examination process.

Meanwhile, besides the patient image and the medical examination data, when survey about the symptom or suspected disease is performed, the communication unit 130 may transmit at least one of the survey and the reply to the survey to an external device.

The camera 150 may capture an image of the patient while the questionnairing process is performed, and in this case, the communication unit 130 may transmit the patient image captured during the questionnaring process to an external device. Here, the external device may include the doctor's terminal 10, the medical server 20, or the like. When the information is transmitted to the doctor's terminal, the doctor's terminal 10 may provide the information to the doctor, to allow the doctor to perform a medical determination based on the information.

Here, the communication unit 130 may transmit the entirety of a portion of the images of the patient to the external device. The entirety of the images of the patient may refer to all the images captured during the self-examination process.

Also, the portion of the images of the patient may refer to images of the patient regarding a partial time interval during the self-examination. For example, when 30 minutes are taken for the medical examination process, 10 minutes may be required for the actual medical examination with the medical examination instrument 30. A portion of the images of the patient may be images during the actual medical examination performed in the course of the entire medical examination process. The controller 160 may edit the entirety of the captured images of the patient as the foregoing portion.

For example, the controller 160 may collect only the images while medical examination data is being received from the medical examination instrument 30 among the images of the patient captured by the camera, and accordingly, the portion of the images of the patient can be obtained. Thus, the doctor's terminal 10 can provide the images of the patient corresponding to a time interval required by the doctor, rather than the entire self-examination process, whereby the doctor can treat the patient more quickly.

Also, a portion of the patient image may be an image of a portion of the entire area of the patient image. For example, as shown in FIG. 21, the controller 160 may obtain a portion of the patient image, excluding a portion of the entire area of the patient image. The communication unit 130 may transmit the portion of the patient image. For example, the controller 160 may edit the patient image by deleting an area excluding the portion medically required by the doctor. Or, the input unit 110 may receive an input selecting a portion of the entire area of the patient image, and the controller 160 may edit the patient image accordingly.

The method for the self-examination according to the third exemplary embodiment of the present invention has the effect that because the self-examination results are transmitted by the apparatus for the self-examination to an external device, the doctor can determine the patient's disease with reference to the self-examination results.

Also, because the patient transmits the process of performing the self-examination together, the doctor can more clearly check the medical examination results.

Also, because the doctor receives the medical examination results in advance before a face-to-face treatment (i.e., clinic-based consultation) or a telemedicine (i.e., teleconsultation), time and cost required and incurred for the medical treatment can be reduced. In addition, because the medical examination results are provided to the patient, the patient can immediately check his physical condition.

The methods for the self-examination according to the respective exemplary embodiments of the present invention can be used alone or may be combined to be used. The steps constituting the respective exemplary embodiments may be used alone or may be combined with the steps constituting the other exemplary embodiments so as to be used.

The preferred embodiments of the present invention have been described with reference to the accompanying drawings, and it will be apparent to those skilled in the art that various modifications and variations can be made in the present invention without departing from the scope of the invention. Thus, it is intended that any future modifications of the embodiments of the present invention will come within the scope of the appended claims and their equivalents.

INDUSTRIAL APPLICABILITY

In the apparatus and the method for the self-examination according to the present invention, because medical examination guide information including a body part for performing the self-examination according to a symptom and a suspected disease is provided to the user, the user can examine himself by using a medical examination instrument.

The invention claimed is:
1. An apparatus for a self-examination comprising:
an input unit;
a camera configured to capture a patient image of a user;
a display configured to display the patient image;
a communication unit; and
a controller configured to:
  display a survey for at least one of a symptom and a suspected disease,
  receive a reply to the survey through the input unit,
  obtain medical examination guide information for a plurality of body parts based on the reply to the survey, wherein the medical examination guide information includes information of the plurality of body parts, a type of the medical examination instrument to be used for the self-examination and information for guiding manipulation of the medical examination instrument,
determine a plurality of positions corresponding to the plurality of body parts on the patient image for the self-examination,
determine an examination order for examining the plurality of body parts based on the medical examination guide information,
display a plurality of icons based on the examination order for the self-examination on the patient image at the plurality of positions corresponding to the plurality of body parts,
determine a position of a medical examination instrument based on position information received through the communication unit or the patient image,
display a message indicating the medical examination instrument is at a correct position based on the examination order or a guide message indicating a direction and a distance for moving the medical examination instrument to the correct position based on the examination order,
receive, via the communication unit, medical examination data for one of the plurality of body parts from the medical examination instrument which obtains the medical examination data from the one of the plurality of body parts,
determine a presumed disease based on at least one of the symptom, the suspected disease and the medical examination data, and
display information regarding a hospital within a predetermined range based on a location of the user available for treatment of the presumed disease.

2. The apparatus of claim 1, further comprising:
a storage unit configured to store medical examination information of respective symptoms,
wherein the controller obtains the medical examination guide information based on at least one medical examination information corresponding to the symptom according to the reply, among the medical examination information of the respective symptoms.

3. The apparatus of claim 1, wherein the controller determines the suspected disease based on the symptom according to the reply and obtains the medical examination guide information based on the suspected disease.

4. The apparatus of claim 3, further comprising:
a storage unit configured to store medical examination information of respective diseases,
wherein the controller obtains the medical examination guide information based on at least one medical examination information corresponding to the suspected disease among the medical examination information of the respective diseases.

5. The apparatus of claim 1,
wherein the controller receives, via the input unit, the suspected disease.

6. The apparatus of claim 1, wherein the controller receives, via the communication unit, the suspected disease from an external device.

7. The apparatus of claim 1, wherein the medical examination guide information includes information of the medical examination instrument, and
wherein when the medical examination instrument from which the apparatus received the medical examination data is different from the medical examination instrument according to the medical examination guide information, the controller controls the output unit to output an error message.

8. The apparatus of claim 1, wherein when the medical examination instrument is on a body part among the plurality of body parts, the controller controls the output unit to output an alarm message.

9. The apparatus of claim 1, wherein the medical examination guide information includes precautions for the self-examination, and the controller controls the output unit to output the precautions for the self-examination.

10. The apparatus of claim 1, wherein the controller transmits, via the communication unit, the medical examination data to an external device.

11. The apparatus of claim 10, further comprising:
a storage unit configured to store the patient image and the medical examination data.

12. The apparatus of claim 11, wherein the controller transmits, via the communication unit, at least one of the patient image and an edited patient image, and
wherein the edited patient image includes at least one of an image of a partial area of an entire area of the patient image and an image taken during a partial time interval of an entire time interval.

13. A method for a self-examination, the method comprising:
displaying a survey for at least one of a symptom and a suspected disease;
receiving, via an input unit, a reply to the survey;
obtaining, via a controller, medical examination guide information for a plurality of body parts based on the reply to the survey, wherein the medical examination guide information includes information of the plurality of body parts, a type of the medical examination instrument to be used of the self-examination and information for guiding manipulation of the medical examination instrument;
displaying, via the output unit, a patient image of a user being captured by a camera;
determining a plurality of positions corresponding to the plurality of body parts on the patient image for the self-examination;
determining an examination order for examining the plurality of body parts based on the medical examination guide information;
displaying a plurality of icons for the self-examination on the patient image at the plurality of positions corresponding to the plurality of body parts;
determining a position of a medical examination instrument based on position information received through the communication unit or the patient image;
displaying a message indicating the medical examination instrument is at a correct position based on the examination order or a guide message indicating a direction and a distance for moving the medical examination instrument to the correct position based on the examination order;
receiving, via a communication unit, medical examination data for one of the plurality of body parts from the medical examination instrument, wherein the medical examination instrument obtains the medical examination data from the one of the plurality of body parts;
determining a presumed disease based on at least one of the symptom, the suspected disease and the medical examination data; and displaying information, regarding a hospital within a predetermined range based on a location of the user available for treatment of the presumed disease.

14. The method of claim 13, further comprising:
storing the patient image and the medical examination data.

15. The method of claim 14, further comprising:
transmitting, via the communication unit, at least a portion of the patient image and the medical examination data to an external terminal.

* * * * *